United States Patent
Meuser et al.

(10) Patent No.: US 9,351,912 B2
(45) Date of Patent: May 31, 2016

(54) COMPOSITION FOR KERATIN FIBERS

(75) Inventors: Alexandra Meuser, Egelsbach (DE); Huma Younas, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 14 days.

(21) Appl. No.: 14/112,371

(22) PCT Filed: Mar. 30, 2012

(86) PCT No.: PCT/EP2012/055811
§ 371 (c)(1),
(2), (4) Date: Oct. 17, 2013

(87) PCT Pub. No.: WO2012/150098
PCT Pub. Date: Nov. 8, 2012

(65) Prior Publication Data
US 2014/0044665 A1 Feb. 13, 2014

(30) Foreign Application Priority Data

May 2, 2011 (EP) .................................... 11164429

(51) Int. Cl.
| | | |
|---|---|---|
| A61K 8/46 | (2006.01) | |
| A61K 8/44 | (2006.01) | |
| A61Q 5/10 | (2006.01) | |
| A61K 8/49 | (2006.01) | |
| A61K 8/81 | (2006.01) | |
| A61Q 5/00 | (2006.01) | |
| A61K 8/64 | (2006.01) | |
| A61K 8/86 | (2006.01) | |
| A61Q 5/06 | (2006.01) | |
| A61Q 5/08 | (2006.01) | |

(52) U.S. Cl.
CPC . *A61K 8/466* (2013.01); *A61K 8/44* (2013.01); *A61K 8/49* (2013.01); *A61K 8/64* (2013.01); *A61K 8/8152* (2013.01); *A61K 8/86* (2013.01); *A61Q 5/002* (2013.01); *A61Q 5/10* (2013.01); *A61K 2800/882* (2013.01); *A61Q 5/065* (2013.01); *A61Q 5/08* (2013.01)

(58) Field of Classification Search
None
See application file for complete search history.

(56) References Cited

FOREIGN PATENT DOCUMENTS

| | | |
|---|---|---|
| EP | 0 529 437 A1 | 3/1993 |
| EP | 2 201 931 A1 | 6/2010 |
| EP | 2 201 932 A1 | 6/2010 |
| EP | 2 201 933 A1 | 6/2010 |
| EP | 2201931 A1 * | 6/2010 |
| EP | 2 314 278 A1 | 4/2011 |
| JP | 2006 160641 A | 6/2006 |
| WO | 99 22701 A1 | 5/1999 |
| WO | WO-2010018668 A1 * | 2/2010 |

OTHER PUBLICATIONS

Handbook of Plastic and Rubber Additives. Second Edition, vol. 1-2. Chemical Component Cross-Reference. p. 1047. 2005.*
International Search Report Dated Apr. 18, 2013, Mailed May 2, 2013.

* cited by examiner

*Primary Examiner* — Amber D Steele
*Assistant Examiner* — Schuyler Milton
(74) *Attorney, Agent, or Firm* — Norris McLaughlin & Marcus PA

(57) ABSTRACT

Present invention relates to a composition for keratin fibers especially for human hair comprising glycylglycine and/or its derivatives, an aromatic sulphonic acid and/or its salts and an anionic polymer for improving cosmetic properties of hair such as volume, body, elasticity and curl retention.

15 Claims, No Drawings

COMPOSITION FOR KERATIN FIBERS

This application is a 371 application of PCT/EP2012/05581 filed Mar. 30, 2012, which claims foreign priority benefit under 35 U.S.C. §119 of European Application No. 11164429.0 filed May 2, 2011.

Present invention relates to a composition for keratin fibers especially for human hair comprising glycylglycine and/or its derivatives, an aromatic sulphonic acid and/or its salts and an anionic polymer for improving cosmetic properties of hair such as volume, body, elasticity and curl retention.

Hair volume, body, elasticity and curl retention have often been addressed as part of the problems dealt with improving cosmetic appearance of human hair. Various attempts have been made to solve all or part of the problems with various types of compositions. It has been know to use polymer comprising compositions after cleansing and or conditioning hair in order to give a style to hair which includes increasing hair volume by setting. These types of compositions are not rinsed off from hair after application.

On the other hand, conditioning compositions are applied onto hair in order to improve cosmetic properties of hair such as combability, shine, elasticity, volume and body which are rinsed off after certain period of processing time on hair, do often not deliver the satisfactory results. Therefore there is a great need for new compositions and processes for improving hair volume, elasticity and curl retention in order to increase consumer satisfaction.

It is known from Kao Corporations patent application published under the number EP 2 201 931 A1 that use of sulphonic acid and/or its salts in combination with glycylglycine and/or its derivatives improves hair softness and imparts hair volume and body and bounce. It has further been disclosed in the said application that such compositions comprise additionally cationic polymers. Nothing is disclosed on further improvement of hair volume, body, curl retention and elasticity by inclusion of an anionic polymer into such composition.

It has surprisingly been found out that an aqueous composition comprising an aromatic sulphonic acid and/or its salt, glycylglycine and/or its derivative and an anionic polymer improves hair volume, body, curl retention and elasticity of keratin fibers especially human hair independent from its physical status such as damaged or healthy hair. It has especially been observed that a homogeneous improvement of all said properties is achieved on keratin fibers which improve parts with various damage levels from previous chemical treatments and/or environmental effects.

Accordingly, the first object of the present invention is an aqueous composition comprising an aromatic sulphonic acid and/or its salt, glycylglycine and/or its derivative and an anionic polymer.

Second object of the present invention is the use of aqueous composition of the present invention for improving volume, body, curl retention and elasticity of keratin fibers especially human hair.

Third object of the present invention is process for treating keratin fibers especially human hair and especially for improving hair volume, body, curl retention and/or elasticity wherein an aqueous composition of the present invention is applied onto hair and after processing of 1 to 45 min at ambient temperature of in a temperature range of 20 to 45° C. rinsed off from hair.

Still another object of the present invention is a kit for keratin fibers especially human hair comprising two or more compositions wherein at least one of the compositions is an aqueous composition of the present invention.

Composition of the present invention is an aqueous composition and comprises at least 50% by weight calculated to total composition water.

Aqueous composition of the present invention comprises at least one aromatic sulphonic acid and/or its salt. With the term aromatic sulphonic acid it is meant that the compound comprises at least one aromatic ring, preferably a phenyl ring which may further be substituted and/or fused with another ring structure.

Preferred aromatic sulphonic acid compounds are benzenesulphonic acid, para-toluenesulfonic acid, 2,4-dimethylbenzenesulfonic acid, 2,5-dimethylbenzenesulfonic acid, naphthalenesulfonic acid and saccharin and their salts. More preferred are paratoluenesulfonic acid and/or a salt thereof, 2,4-dimethylbenzenesulfonic acid and/or a salt thereof, naphthalenesulfonic acid and/or a salt thereof, and saccharin and/or a salt thereof. The most preferred are paratoluenesulfonic acid and/or a salt thereof and/or naphthalenesulfonic acid and/or a salt thereof.

Concentration of aromatic sulphonic acid compound and their respective salts in the aqueous compositions of the present invention is in the range of 0.1 to 20% and preferably 0.2 to 15%, more preferably 0.3 to 10% and most preferably 0.5 to 7.5% by weight calculated to the total of the composition.

Aqueous composition of the present invention comprises glycylglycine and/or it derivative and/or their salts which may also be present in the compositions as a zwitterionic compound.

Suitable and preferred compounds are gylcylglycine, glycylglycylglycine and a compound according to the following structures of G1 to G9.

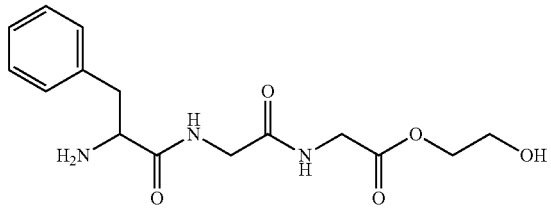

(G1)

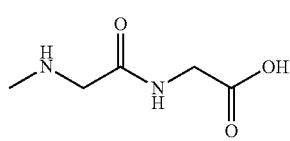

(G2)

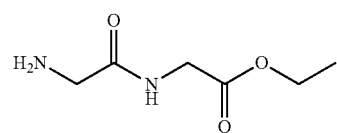

(G3)

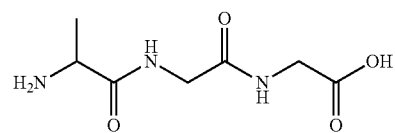

(G4)

-continued

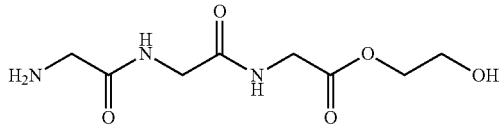
(G5)

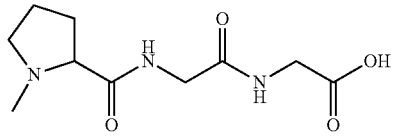
(G6)

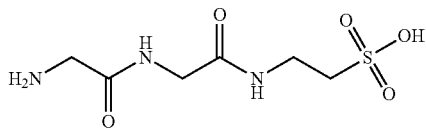
(G7)

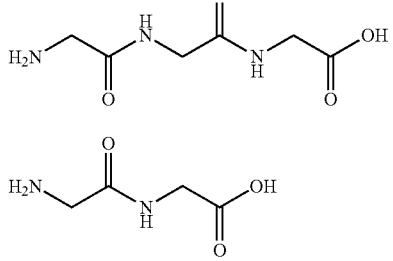
(G8)

(G9)

Most preferred are glycylglycine and/or its salts such as salts with inorganic acids for example hydrochloric acid, sulphuric acid, and with organic acids for example with lactic acid and salts with alkali compounds such as ammonium salt and alkyl ammonium salt and alkali metal salts such as sodium and potassium salts.

Concentration of glycylglycine and/or its derivatives and their respective salts in the aqueous compositions of the present invention is in the range of 0.01 to 10% and preferably 0.02 to 7.5%, more preferably 0.05 to 5% and most preferably 0.1 to 3% by weight calculated to the total of the composition.

Aqueous composition of the present invention comprises an anionic polymer. Suitable anionic polymers must preferably have a thickening effect on aqueous composition and more preferably the anionic polymer is selected from Aqueous composition of the present invention comprises thickening acrylate polymers.

Non-limiting suitable ones are acrylates/aminoacrylates/C10-30 alkyl PEG-20 itaconate copolymer, acrylates ammonium methacrylate copolymer, acrylates/beheneth-25 methacrylate copolymer, acrylates/C10-30alkylacrylate crosspolymer, acrylates/ceteth-20 methacrylate copolymer, acrylates/ceteth-20 itaconate copolymer, acrylates/laureth-25 methacrylate copolymer, acrylates copolymer and acrylates/palmeth-25 acrylate copolymer and acrylates/steareth-20 methacrylate copolymer. Most preferred is known with the CTFA adopted name acrylates copolymer and commercially available under the trade names such as Carbopol Aqua SF-1 from Noveon and Aculyn 33A from Rohm and Haas.

Concentration of anionic polymer in the aqueous compositions is in the range of 0.05 to 5%, preferably 0.1 to 4%, more preferably 0.2 to 3% and most preferably 0.25 to 2% by weight calculated to the total of the composition.

pH of the aqueous composition of the present invention is in the range of 2 to 11, preferably in the range of 5 to 10, more preferably in the range of 6 to 10 and most preferably in the range of 6.8 to 10 and in particular pH of the composition is alkaline and in the range of 8 to 10.

In the preferred form of the present invention aqueous composition comprises at least one alkalizing agent preferably selected from ammonium hydroxide and amines according to the following general structure $$R_1R_2R_3N$$

wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is different from H.

Suitable alkanolamines according to the general formula of above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

Within the meaning of the present invention it should also be understood that aqueous compositions can comprise more than one alkanolamine such as a mixture of two or three alkanolamines.

The concentration of at least one alkanolamine in the compositions varies between 1 and 35%, preferably 1 and 30, more preferably 2.5 and 25 and most preferably 2.5 to 20% by weight calculated to the total of the composition.

In a preferred form of the present invention the aqueous composition comprises one or more hair dyes. Hair dyes are preferably selected from direct dyes and oxidative dyes precursors. Suitable oxidative dye precursor, also called developer, are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2- methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The composition according to the invention optionally comprises at least one coupling substance in case a oxidative dye precursor is comprised in the composition. Suitable non-limiting examples to the coupling substances are resorcinol, 2-methyl resorcinol, 4-chlororesorcinol, 2-amino-4-chlorophenol, 5-amino-4-methoxy-2-methylphenol, 3-aminophenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

A hair direct dye is also comprised in the compositions of the present invention. Suitable ones are cationic, anionic and nitro dyes. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

According to the invention, the coloring composition comprises dyes at a total concentration of 0.01 to 10%, preferably 0.05 to 7.5%, more preferably 0.1 to 5% by weight calculated to total composition.

Aqueous composition of the present invention may be in the form of gel, solution, thickened solution, emulsion or multiphase composition which is mixed to homogeneity prior to application onto hair. In case aqueous composition is in the form of a gel, composition comprises at least one gelling agent in addition to the anionic polymer already present in the composition. Compatibility must be evaluated prior to the selection of the thickening polymer. Generally suitable ones are for example nonionic polysaccharide thickeners such as xanthan gum, cellulosic polymers which may comprise various substitutes such as an alky or hydroxyl alkyl chains.

Emulsion compositions comprises preferably at least one fatty alcohol of the general formula

$R_4$—OH wherein $R_4$ is a linear or branched, saturated or unsaturated alkyl chain with 12 to 22 C atoms and at least one emulsifier selected from anionic, non-ionic, cationic and amphoteric surfactants.

Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 2.5 to 20%, more preferably 5 to 15% and most preferably 5 to 10% by weight calculated to total composition.

The composition of the present invention comprises at least one emulsifier selected from anionic, non-ionic, cationic and amphoteric surfactants. Preferred emulsifying surfactants are anionic and non-ionic ones and especially preferred are the mixture of non-ionic surfactants.

In principal any anionic surfactant is suitable within the meaning of the present invention. Nonlimiting examples are anionic surfactants of the sulfate, sulfonate, carboxylate and alkyl phosphate type, especially, of course, those customarily used as emulsifiers, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates and their salts.

Further suitable surfactants of the carboxylate type are alkyl polyether carboxylic acids and the salts thereof of the formula $$R_5-(C_2H_4O)_n-O-CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_5-\underset{\underset{O}{\|}}{C}-\underset{\underset{H}{|}}{N}-CH_2-CH_2-(C_2H_4O)_n-CH_2COOX$$

wherein $R_5$ and X have the above meanings, and n is in particular a number from 1 to 10, preferably 2.5 to 5.

Among the anionic surfactants most preferred are alkyl sulfates and/or alkyl ether sulfates and among them sodium lauryl or laureth sulfates and their mixtures are most preferred.

Suitable non-ionic surfactants are alkyl polyglucosides of the general formula $$R_6-O-(R_7O)_n O-Z_x$$

wherein $R_6$ is an alkyl group with 8 to 18 carbon atoms, $R_7$ is an ethylene or propylene group, Z is a saccharide group with 5 to 6 carbon atoms, n is a number from 0 to 10 and x is a number between 1 and 5. Examples are decyl polyglucoside and cocoyl polyglucoside, both beeing commercially available.

Further nonionic surfactant components are, for example, long-chain fatty acid mono- and dial kanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Among the non-ionic surfactants mentioned above fatty alcohol ethoxylates and fatty acid alkanolamides and their mixtures at any weight ratio are the most preferred ones.

Although less preferred because of possible compatibility problem with anionic polymer required for the compositions of the present invention, if cationic surfactant is compatible with the rest of the composition it may be comprised in the compositions of the present invention. As a rule any mono alkyl quaternary ammonium surfactants is suitable for the compositions of the present invention as cationic emulsifying surfactant. With the term mono alkyl it is meant that quaternary ammonium surfactant includes only one alkyl chain which has more than 8 C atoms. The term does not exclude that the quaternary ammonium surfactant includes further short alkyl chains, $C_1$ to $C_4$, present in the molecule.

Preferably at least one mono alkyl quaternary ammonium surfactant is selected from the compounds with the general formula $$R_{10}-\underset{\underset{R_{11}}{|}}{\overset{\overset{R_8}{|}}{N^+}}-R_9 \quad X^-$$

where $R_8$ is saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 0-4 or $$R_{12}COO(CH_2)_n$$

where $R_{12}$ is saturated or unsaturated, branched or non-branched alkyl chain with 7-21 C atoms and n has typical value of 0-4, and $R_9$, $R_{10}$ and $R_{11}$ are independent from each other lower alkyl chain with 1 to 4 carbon atoms, hydroxyl alky chain with 1 to 4 C atoms, or ethoxy or propoxy group with number of ethoxy or propoxy groups varying in the range of 1 to 4, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, stear trimonium chloride, stearamidopropyltrimethylammonium chloride, stearamidopropyl trimonuim chloride.

Surfactants are included into the aqueous composition of the present invention at a total concentration of 0.5 to 20%, preferably 1 to 15% and most preferably 2-10%, and most preferably 2 to 7.5% by weight, calculated to the total composition.

Composition of the present invention preferably comprises at least one oxidizing agent at a concentration of 1 to 12% by weight calculated to of the composition, especially when the composition comprises oxidative dye precursors and optionally coupling agent which may optionally be combined with a hair dye. Suitable and most preferred oxidizing agent is hydrogen peroxide.

It must be noted that in case that the aqueous compositions of the present invention is used for hair colouring, composition is divided into two parts wherein the first part comprises dyeing agents and the second part comprises oxidizing agent which are mixed immediately before application onto hair. This belongs to the general knowledge of the skilled worker and also disclosed in the above referred patent application of Kao Corporation.

Furthermore, compositions of the present invention may be mixed with an anhydrous composition comprising at least one persalt for the purpose of bleaching. In such a case, a three part composition must be mixed immediately before application onto hair wherein the first composition is a composition according to the present invention, the second composition is an aqueous composition comprising ate least one oxidizing agent and the third composition being anhydrous composition comprising at least one persalt.

In an another preferred from of the present invention is that anionic polymer is added to the aqueous composition comprising aromatic sulphonic acid and/or its salt and glycylglycine and/or its derivative at the time of use which may be found advantageous in terms of storage stability. Accordingly, another object of the present invention is a process for treating hair wherein an aqueous composition comprising aromatic sulphonic acid and/or its salt and glycylglycine and/or its derivative is added an anionic polymer immediately prior to use and applied onto hair and after processing of 1 to 45 min at ambient temperature of in a temperature range of 20 to 45° C. rinsed off from hair.

Composition of the present invention may comprise furthermore compounds customarily found in a cosmetic composition such as fragrance, reducing agents, lipids, chelating agents, solubilizers, vitamins, proteins and their hydrolyzates, moisturizing agents such as polyols.

Following examples are to illustrate the invention but not to limit it.

EXAMPLE 1

|   | % by weight |
|---|---|
| p-Toluenesulphonic acid | 0.99 |
| Glycylgylcine | 0.33 |
| Acrylates copolymer* | 0.45 |
| Monoethanolamine | q.s to pH 8.0 |
| Water | q.s. to 100 |

*Carbopol Aqua SF 1

Above composition was prepared by dissolving p-toluenesulphonic acid and glycylglycine in water and combining it with the dispersion of acrylates copolymer in water and finally pH of the composition was adjusted to 8.0.

A hair streak was treated with the above composition at room temperature for 30 min and hair was rinsed off with water and shampooed once. It was observed that the streak had better curl retention determined after 24 h that a hair streak treated with the same composition but without acrylates copolymer.

Curl retention was determined under ambient conditions. Hair streaks treated with the compositions (inventive and comparative composition without acrylates copolymer) wound on a curler in wet stage and heated with a hair dryer at an approximate temperature of 75° C. for 10 min and released from curler. The length of the curly hair was measured after 24 h and compared to the initial length of the hair. It was observed that length of curly hair was shorter for the streak treated with the inventive composition than the one treated with the comparative composition.

EXAMPLE 2

|   | % by weight |
|---|---|
| Hair dyeing composition | |
| Cetearyl alcohol | 10.8 |
| Oleth-5 | 5.0 |
| Oleic acid | 2.5 |
| p-Toluenesulphonic acid | 2.40 |
| Glycylgylcine | 0.90 |
| Stearamide MEA | 2.3 |
| Cocamide MEA | 2.3 |

-continued

|   | % by weight |
|---|---|
| Sodium cetearyl sulfate | 1.0 |
| Propylene glycol stearate | 0.6 |
| Sodium lauryl sulfate | 0.5 |
| Sodium sulfite | 1.0 |
| Triethanolamine | 8.0 |
| Toluene 2,5-diamine sulfate | 0.6 |
| 2-Methylresorcinol | 0.2 |
| Resorcinol | 0.1 |
| 2-Amino-3-hydroxypyridine | 0.05 |
| 2,5,6-Triamino-4-pyrimidinol sulfate | 0.02 |
| Water | q.s. to 100 |
| Oxidizing composition | |
| Hydrogen peroxide | 6.0 |
| Cetearyl alcohol | 1.7 |
| Sodium lauryl sulfate | 0.2 |
| Phosphoric acid | 0.3 |
| Salicylic acid | 0.01 |
| Simethicone | 0.002 |
| Water | q.s. to 100 |

17 g of the above dyeing composition was mixed with 17 g of the oxidizing composition and 0.5 g of acrylates copolymer (Carbopol Aqua SF 1) was mixed into the composition. So obtained composition was applied onto a persons hair and processed 30 min at approximately 40° C. and afterwards hair was rinsed off with water and dried with a hair drier. It was observed that hair had improved elasticity, manageability, was well combable and had improved body and volume.

The invention claimed is:

1. An aqueous composition for keratin fibers, comprising an aromatic sulphonic acid and/or its salt; glycylglycine and/or its derivative; and an anionic polymer present at a concentration in the range of 0.1 to 5% by weight calculated to the total of the composition, wherein the aqueous composition is alkaline.

2. The composition according to claim 1, wherein the aromatic sulphonic acid and/or its salt is selected from the group consisting of benzenesulphonic acid, para-toluenesulfonic acid, 2,4-dimethylbenzenesulfonic acid, 2,5-dimethylbenzenesulfonic acid, naphthalenesulfonic acid and saccharin, and their salts.

3. The composition according to claim 1, wherein aromatic sulphonic acid and/or its salt is paratoluenesulfonic acid and/or a salt thereof, and/or naphthalenesulfonic acid and/or a salt thereof and is present at a concentration in the range of 0.1 to 20% by weight calculated to the total of the composition.

4. The composition according to claim 1, wherein the glycylglycine and/or its derivative is selected from the group consisting of glycylglycine, glycylglycylglycine and a compound according to one of the following structures of G1 to G9

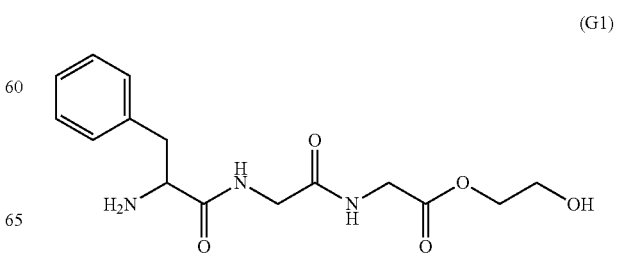

(G1)

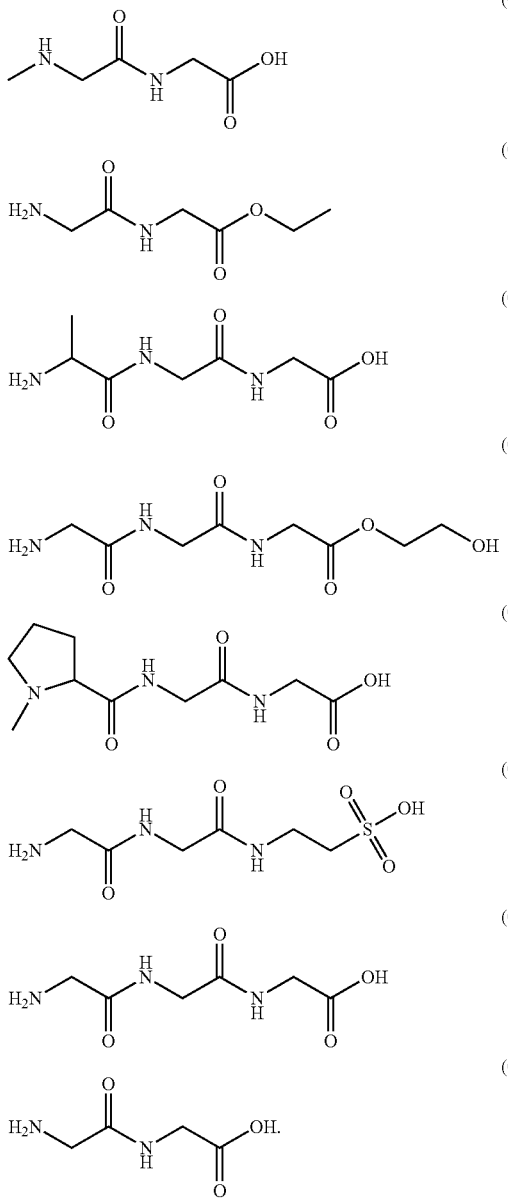

5. The composition according to claim 1, wherein the glycylglycine and/or its derivative is glycylglycine and/or its salts chosen from the group consisting of hydrochloric acid, sulphuric acid, lactic acid, ammonium salt, and alkyl ammonium salt, sodium salts and potassium salts and is present at a concentration in the range of 0.1 to 10% by weight calculated to the total of the composition.

6. The composition according to claim 1, wherein the anionic polymer is a thickening acrylate polymer and is selected from the group consisting of acrylates/aminoacrylates/C10-30 alkyl PEG-20 itaconate copolymer, acrylates ammonium methacrylate copolymer, acrylates/beheneth-25 methacrylate copolymer, acrylates/C10-30alkylacrylate crosspolymer, acrylates/ceteth-20 methacrylate copolymer, acrylates/ceteth-20 itaconate copolymer, acrylates/laureth-25 methacrylate copolymer, acrylates copolymer and acrylates/palmeth-25 acrylate copolymer and acrylates/steareth-20 methacrylate copolymer.

7. The composition according to claim 1, wherein it comprises at least one alkalizing agent selected from ammonia and a compound according to the general structure $$R_1R_2R_3N$$

wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is different from H.

8. The composition according claim 1, wherein it comprises hydrogen peroxide at a concentration of 1 to 12% by weight calculated to the total of the composition.

9. The composition according to claim 1, wherein it comprises a hair dye.

10. The composition according to claim 1, wherein it comprises at least one fatty alcohol and/or at least one emulsifier selected from anionic, nonionic, cationic and amphoteric surfactants.

11. A process for treating keratin fibers, wherein a composition according to claim 1 is applied onto the keratin fibers and after processing of 1 to 45 min at ambient temperature in a range of 20 to 45° C., is rinsed off from the keratin fibers.

12. A kit for keratin fibers, comprising two or more compositions wherein at least one of the compositions is a composition according to claim 1.

13. The composition according to claim 1, wherein the keratin fibers are human hair.

14. The process according to claim 11, wherein the keratin fibers are human hair, and wherein the process is for treating human hair, or for improving human hair volume, body, curl retention and/or elasticity.

15. The kit according to claim 12 wherein the keratin fibers are human hair.

* * * * *